United States Patent [19]
Motion et al.

[11] Patent Number: 5,068,466
[45] Date of Patent: Nov. 26, 1991

[54] CYMENOL PREPARATION BY TRANSFER DEHYDROGENATION

[75] Inventors: Keith R. Motion, Hythe; Christopher P. Newman, Canterbury, both of Great Britain

[73] Assignee: Unilever Patent Holdings B.V., Rotterdam, Netherlands

[21] Appl. No.: 578,495

[22] Filed: Sep. 6, 1990

[30] Foreign Application Priority Data

Sep. 6, 1989 [GB] United Kingdom ................. 8920109

[51] Int. Cl.$^5$ ............................................. C07C 39/06
[52] U.S. Cl. .................................... 568/781; 568/782
[58] Field of Search ................... 512/20, 25; 568/715, 568/814, 830, 782, 781

[56] References Cited

U.S. PATENT DOCUMENTS

| | | | |
|---|---|---|---|
| 2,361,532 | 10/1944 | Cox | 568/814 |
| 2,366,409 | 1/1945 | Johnston | 568/814 |
| 2,743,300 | 4/1956 | Joris . | |
| 2,881,220 | 4/1959 | Griffin . | |

FOREIGN PATENT DOCUMENTS 0047478 1/1918 Finland ............................... 568/814

OTHER PUBLICATIONS

Brieger et al., Catalytic Transfer Hydrogenation, Chemical Reviews, vol. 74, No. 5, 1974.
Arctander, "Perfume and Flavor Chemicals", vol. II, 1969, Pub. by Author, Montclair, N.J., TP983 A8C.

*Primary Examiner*—Werren B. Lone
*Attorney, Agent, or Firm*—Cushman, Darby & Cushman

[57] ABSTRACT

The invention relates to a process for the conversion of 8-hydroxymenthenes into 8-hydroxycymenes by reacting the 8-hydroxymenthenes in the liquid phase in the presence of a dehydrogenation catalyst, e.g. palladium and a hydrogen acceptor e.g. mesityl oxide. The process is preferably carried out at 80°–150° C. and in the presence of base. The process is particularly suitable for converting 8-hydroxy-p-menth-1-ene into 8-hydroxy-p-cymene. The reaction products are of value as intermediates in the preparation of fragrance chemicals.

9 Claims, No Drawings

CYMENOL PREPARATION BY TRANSFER DEHYDROGENATION

FIELD OF THE INVENTION

The present invention relates to the production of 8-hydroxycymenes which are of value as intermediates in the preparation of fragrance chemicals.

In particular, this invention relates to improvements in the production of intermediates suitable for the preparation of fragrances and, in particular, to improvements in the production of 8-hydroxycymenes.

BACKGROUND OF THE INVENTION

An important substance in the preparation of fragrances in the musk field is 7-acetyl-1,1,3,4,4, 6-hexamethyltetralin. This substance has excellent odour and fixative properties. It is stable to alkali and light, soluble in most solvents, substantially colourless and persistent and is also relatively cheap. It is commonly prepared by acetylation of hexamethyltetralin in a Friedel-Crafts reaction. In turn, many routes have been proposed for the preparation of this latter substance. Several have been proposed involving the formation of an alicyclic attachment to substituted cymenes which in turn may be obtained from 8-hydroxycymene.

It is known from US 2 366 409 (Hercules) that 8-hydroxymenthene can be converted to a mixture of 8-hydroxycymene and 8-hydroxymenthane by means of a disproportionation reaction. This reaction appears to be a combination of hydrogenation and dehydrogenation ie. is a tranfer hydrogenation using 8-hydroxymenthene as hydrogen acceptor. For every molecule of 8-hydroxymenthene which is dehydrogenated, enough hydrogen is produced to hydrogenate two molecules of 8-hydroxymenthene. The Hercules reaction results therefore in an approximate 2:1 mixture of respectively 8-hydroxymenthane and 8-hydroxycymene.

BRIEF SUMMARY OF THE INVENTION

We have found that the yield of the desired product, 8-hydroxycymene, can be substantially increased by using an added hydrogen acceptor, and by carrying out the reaction at a temperature of around the reflux temperature of the reaction mixture.

Accordingly the invention provides a process for the conversion of 8-hydroxymenthenes to 8-hydroxycymenes in which an 8-hydroxymenthene is converted in the liquid phase in the presence of a dehydrogenation catalyst and an added hydrogen acceptor.

DETAILED DESCRIPTION OF THE INVENTION

The starting material for the method in accordance with this invention may be any 8-hydroxymenthene. The carbon structure of the menthenes will be found in Bernthsen, Textbook of Organic Chemistry, Sudborough Revision, 1922 edition D. Van Nostrand Company, New York, page 609 and page 613. The system of numbering the carbon atoms shown there will be utilized herein. It will be appreciated that the methyl group represented by carbon number 7 may be para, ortho or meta with respect to the isopropyl group. 8-Hydroxymenthadienes are included within the term 8-hydroxymenthene.

The hydroxymenthene may be in the form of a pure compound, or it may be in the form of a distillation cut reasonably rich therein. For example, 8-hydroxy-p-menth-1-ene (alpha-terpineol) may be utilized in a fairly pure state, or it may be utilized in the form of ordinary commercial Pine Oil, which is usually a mixture of terpene alcohols. It will be understood that where the 8-hydroxymenthene utilized has the para-menthene configuration, as is the case with 8-hydroxy-p-menthene, the derivatives will have the same para arrangement. Similarly, ortho- and meta-hydroxymenthenes lead to ortho and meta products respectively.

The catalyst is preferably a metal of Group VIII particularly palladium but platinum, ruthenium, rhodium, iridium or osmium may be used and may be supported on e.g. carbon, alumina, $BaSO_4$ or $CaCO_3$. It is important to maintain non-acid conditions during the reaction to inhibit dehydration of any alcohol present. In some cases it is advantageous to include eg. alkali, ammonium or alkaline earth metal hydroxides, carbonates, phosphates or organic bases (e.g. amines) or ion exchange resins. The catalyst and starting materials may be pre-washed with a base solution. The amount of catalyst in the reaction is preferably from 0.0001 to 10%, particularly 0.01 to 0.25% by weight of the reaction mixture.

An added hydrogen acceptor is present in the reaction system, and the desired reaction can be generalised in reaction (1).

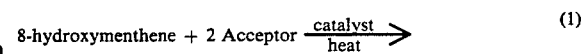

(1)

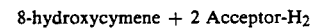

Preferred examples of hydrogen acceptors are molecules for which acceptor-$H_2$ is a product which may be useful in itself. Thus a suitable example of an acceptor is mesityl oxide which is reduced to methyl isobutyl ketone (Acceptor-$H_2$)

Further suitable examples of hydrogen acceptors may be found with reference to G. Brieger and T.J. Nestrick, Chemical Reviews (1974) Vol. 74 No.5 pages 567–580.

The conversion is preferably carried out in the absence of acid, and this may suitably be achieved by the addition of base. When acid is present in the reaction system, dehydration is favoured and the yield of 8-hydroxycymene is decreased.

The conversion is preferably carried out at a temperature near or at the reflux temperature of the reaction mixture, suitably from 80° to 150° C., preferably from 130° to 145° C.

At lower temperatures, for example at less than 80° C., the 8-hydroxymenthene may become the preferred hydrogen acceptor and disproportionation may take place, resulting in unacceptably high levels of 8-hydroxymenthane in the reaction system. If the reaction takes place at higher temperatures, for example over 150° C., the level of cymene may be increased as a result of dehydration/dehydrogenation.

The invention is further illustrated by the following Examples:

EXAMPLES

Example 1

A mixture of 8-hydroxy-p-menth-1-ene (15.4 g, 0.1 mol), mesityl oxide (19.6 g, 0.2 mol), 5% by weight palladium on carbon (1.0 g) and sodium carbonate (1.0 g) was stirred under nitrogen, and heated to reflux.

After ten hours, the reaction mixture was allowed to cool and the catalyst was filtered off. Quantitative GLC analysis showed the product mixture to have the following composition:

| Compound | wt/g | mmol | th · yield (%) |
| --- | --- | --- | --- |
| 8-hydroxy-p-cymene | 11.7 | 78 | 78 |
| 8-hydroxy-p-menth-1-ene | 1.4 | 9 | 9 |
| 8-hydroxy-p-menthane | 1.4 | 9 | 9 |
| p-cymene | 0.4 | 3 | 3 |
| α,p-dimethylstyrene | 0.1 | 1 | 1 |
| methyl isobutyl ketone | 15.9 | 159 | 79 |
| mesityl oxide | 4.1 | 42 | 21 |

Example 2

A mixture of 8-hydroxy-p-menth-1-ene (15.4 g, 0.1 mol), mesityl oxide (19.6 g, 0.2 mol), 5% by weight palladium on carbon (0.1 g) and sodium carbonate (0.05 g) was stirred under nitrogen, and heated to reflux. After twenty hours, the reaction mixture was allowed to cool and the catalyst was filtered off. Quantitative GLC analysis showed the product mixture to have the following composition :

| Compound | wt/g | mmol | th · yield (%) |
| --- | --- | --- | --- |
| 8-hydroxy-p-cymene | 12.9 | 86 | 86 |
| 8-hydroxy-p-menth-1-ene | 1.4 | 9 | 9 |
| 8-hydroxy-p-menthane | 0.2 | 1 | 1 |
| p-cymene | 0.5 | 4 | 4 |
| α,p-dimethylstyrene | — | — | — |
| methyl isobutyl ketone | 15.1 | 151 | 75 |
| mesityl oxide | 4.9 | 50 | 25 |

Example 3

A mixture of 8-hydroxy-p-menth-1-ene (15.4 g, 0.1 mol), mesityl oxide (19.6 g, 0.2 mol) and 5% by weight palladium on calcium carbonate (1.0 g) was stirred mechanically and heated to reflux under nitrogen. After eighteen hours, the reaction was allowed to cool and the catalyst was filtered off. Quantatitive GLC analysis showed the product mixture to have the following composition :

| Compound | wt/g | mmol | th · yield (%) |
| --- | --- | --- | --- |
| 8-hydroxy-p-cymene | 10.2 | 68 | 68 |
| 8-hydroxy-p-menth-1-ene | 1.2 | 8 | 8 |
| 8-hydroxy-p-menthane | 3.0 | 19 | 19 |
| p-cymene | 0.7 | 5 | 5 |
| α,p-dimethylstyrene | — | — | — |
| methyl isobutyl ketone | 12.9 | 129 | 64 |
| mesityl oxide | 6.9 | 69 | 35 |

What is claimed is:

1. A process for the conversion of an 8-hydroxymenthene to an 8-hydroxycymene in which the 8-hydroxymenthene is reacted in the liquid phase in the presence of a dehydrogenation catalyst and an added hydrogen acceptor, wherein the conversion is carried out at a temperature of from 80° to 150° C. and in the absence of acid.

2. A process according to claim 1 wherein the 8-hydroxymenthene is 8-hydroxy-p-menth-1-ene.

3. A process as claimed in claims 1 or 2 wherein the dehydrogenation catalyst comprises a metal of Group VIII.

4. A process as claimed in claim 3 wherein the dehydrogenation catalyst comprises palladium.

5. A process as claimed in any preceding claim wherein the hydrogen acceptor is mesityl oxide.

6. A process as claimed in any preceding claim wherein the conversion is carried out at a temperature within a range near to or at reflux.

7. A process as claimed in claim 6 wherein the conversion is carried out at a temperature of from 130° to 145° C.

8. A process as claimed in claim 1 wherein the conversion is carried out in the presence of added base.

9. A process for the conversion of 8-hydroxy-p-menth- 1-ene into 8-hydroxy-p-cymene in which 8-hydroxy-p-menth-1-ene is reacted in the liquid phase in the presence of a dehydrogenation catalyst comprising palladium and mesityl oxide as a hydrogen acceptor, at a temperature of from 130° to 145° C., in the presence of base.

* * * * *